United States Patent
Piel et al.

(10) Patent No.: US 11,346,599 B2
(45) Date of Patent: May 31, 2022

(54) MULTIFUNCTIONAL RADIO FREQUENCY SYSTEMS AND METHODS FOR UV STERILIZATION, AIR PURIFICATION, AND DEFROST OPERATIONS

(71) Applicant: NXP USA, Inc., Austin, TX (US)

(72) Inventors: Pierre Marie Jean Piel, Chandler, AZ (US); Lionel Mongin, Chandler, AZ (US); Paul Richard Hart, Phoenix, AZ (US)

(73) Assignee: NXP USA, Inc., Austin, TX (US)

( * ) Notice: Subject to any disclaimer, the term of this patent is extended or adjusted under 35 U.S.C. 154(b) by 199 days.

(21) Appl. No.: 16/829,021

(22) Filed: Mar. 25, 2020

(65) Prior Publication Data

US 2020/0224960 A1 Jul. 16, 2020

Related U.S. Application Data

(62) Division of application No. 15/721,436, filed on Sep. 29, 2017, now Pat. No. 10,648,728.

(51) Int. Cl.
*F25D 29/00* (2006.01)
*H01J 61/00* (2006.01)
(Continued)

(52) U.S. Cl.
CPC ............. *F25D 29/00* (2013.01); *A61L 9/20* (2013.01); *A61L 9/22* (2013.01); *F25D 17/042* (2013.01); *F25D 21/006* (2013.01); *F25D 23/12* (2013.01); *H01J 61/00* (2013.01); *H05B 6/50* (2013.01); *H05B 6/62* (2013.01); *A61L 2209/11* (2013.01); *F25D 2317/041* (2013.01); *F25D 2317/0417* (2013.01); *F25D 2700/06* (2013.01); *F25D 2700/08* (2013.01); *H03F 1/56* (2013.01); *H03F 3/21* (2013.01); *H03F 2200/387* (2013.01); *H03F 2200/411* (2013.01); *H05H 1/466* (2021.05); *H05H 1/4652* (2021.05); *H05H 2242/20* (2021.05)

(58) Field of Classification Search
CPC ...... F25D 29/00; F25D 17/042; F25D 21/006; F25D 23/12; F25D 2700/06; F25D 2700/08; A61L 9/20; H05B 6/50; H05B 6/62
See application file for complete search history.

(56) References Cited

U.S. PATENT DOCUMENTS

| | | | |
|---|---|---|---|
| 6,784,405 B2 * | 8/2004 | Flugstad | A23L 3/01 219/505 |
| 8,040,068 B2 | 10/2011 | Coumou et al. | |

(Continued)

*Primary Examiner* — Cassey D Bauer

(57) ABSTRACT

Example systems have a defrost system that can receive a first RF signal at a first frequency to defrost a load. An air treatment device can receive a second RF signal at a second frequency and perform an air treatment process. An RF signal source has a power output, and a switching arrangement selectively electrically connects the defrost system and the first air treatment device to the power output of the RF signal source. A controller can electrically connect one of the defrost system and the first air treatment device to the power output of the RF signal source. When the defrost system is electrically connected, the RF signal source outputs the first RF signal at the first frequency, and when the first air treatment device is electrically connected, the RF signal source outputs the second RF signal at the second frequency.

20 Claims, 5 Drawing Sheets

(51) Int. Cl.
  *A61L 9/20*    (2006.01)
  *H05B 6/50*    (2006.01)
  *H05B 6/62*    (2006.01)
  *H05H 1/46*    (2006.01)
  *H03F 1/56*    (2006.01)
  *F25D 23/12*   (2006.01)
  *A61L 9/22*    (2006.01)
  *F25D 21/00*   (2006.01)
  *F25D 17/04*   (2006.01)
  *H03F 3/21*    (2006.01)

(56) References Cited

U.S. PATENT DOCUMENTS

2015/0298086 A1   10/2015   Dong et al.
2016/0345389 A1   11/2016   Torres et al.

* cited by examiner

MULTIFUNCTIONAL RADIO FREQUENCY SYSTEMS AND METHODS FOR UV STERILIZATION, AIR PURIFICATION, AND DEFROST OPERATIONS

CROSS-REFERENCE TO RELATED APPLICATION

This application is a divisional of co-pending, U.S. patent application Ser. No. 15/721,436, filed on Sep. 29, 2017.

TECHNICAL FIELD

Embodiments of the subject matter described herein relate generally to multifunctional apparatuses and methods of using a single source of radio frequency (RF) energy to selectively power different devices within an appliance.

BACKGROUND

Large quantities of fresh food are wasted every year due to improper or inadequate storage. Storing food safely for a time while maintaining quality can usually be accomplished by storing the food at adequately low temperatures (e.g., below −18 degrees Celsius), by limiting the growth of bacteria that can spoil food, and by reducing the presence of organic molecules that accelerate the aging of the food (e.g., acetone). To use food that is being preserved at low temperatures, time is needed to defrost the food by introduction of ambient heat, for example, before it can be cooked and/or consumed.

Adding functions to devices, such as the above functions related to storing and using food, can be cost-prohibitive, as providing each function separately requires additional costly equipment, and the added equipment increases space requirements. In a food storage appliance such as a refrigerator, for example, space used for equipment is not available for food, and the additional equipment increases the cost of the appliance. As a result, devices that add functions desired by consumers tend to be larger and more costly.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
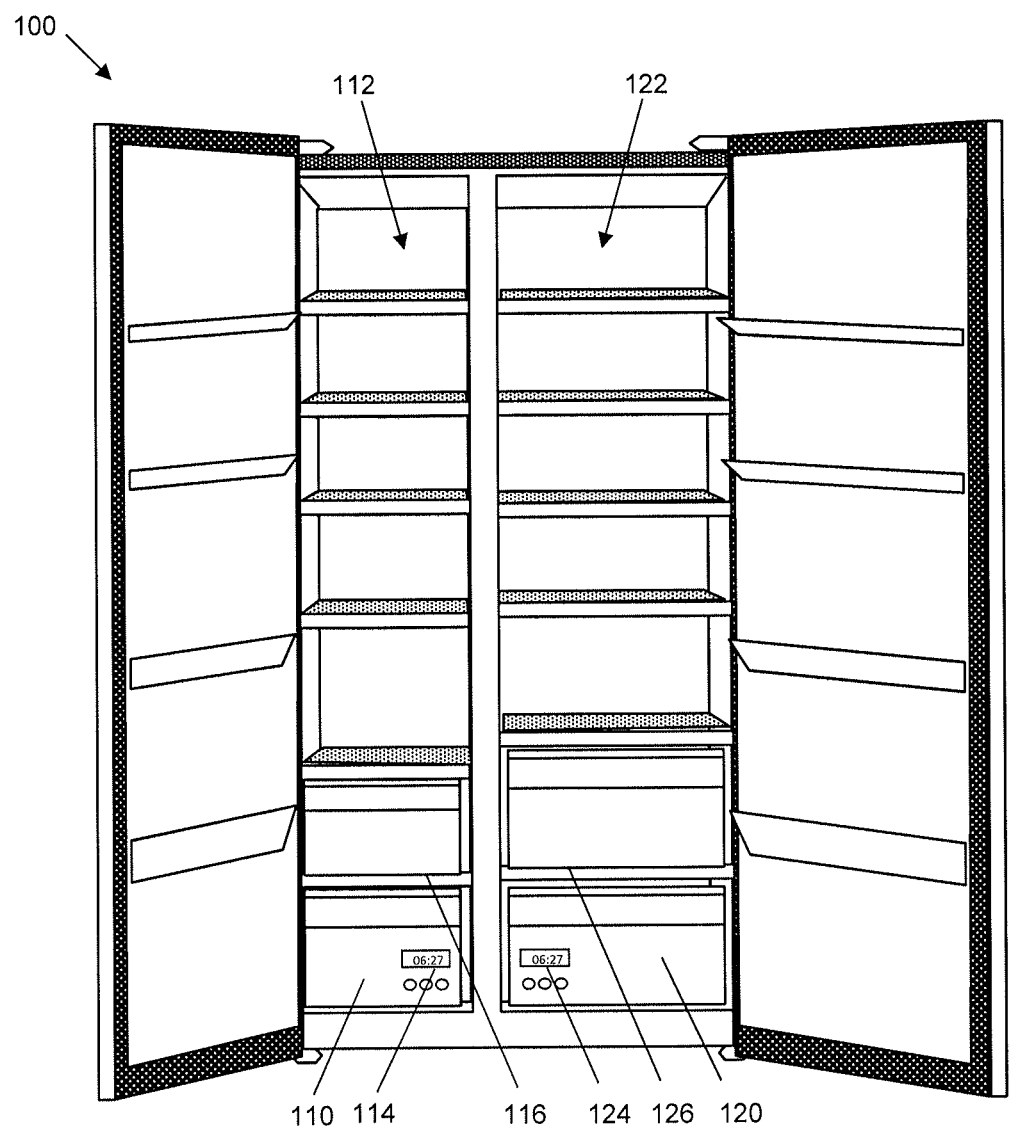
FIG. 1 is a perspective view of a refrigerator/freezer appliance that includes example embodiments of multifunctional systems.

The following detailed description is merely illustrative in nature and is not intended to limit the embodiments of the subject matter or the application and uses of such embodiments. As used herein, the words "exemplary" and "example" mean "serving as an example, instance, or illustration." Any implementation described herein as exemplary or an example is not necessarily to be construed as preferred or advantageous over other implementations. Furthermore, there is no intention to be bound by any expressed or implied theory presented in the preceding technical field, background, or the following detailed description.

Appliances normally perform one function; for example, refrigerators keep food cold. Although appliances with additional functions are generally desirable for consumers, adding functionality tends to make appliances substantially larger and more expensive. Embodiments of the subject matter described herein relate to appliances incorporating multiple devices capable of performing different functions in smaller spaces and at lower costs than would be achievable using conventional techniques. As described in greater detail below, exemplary systems are realized by using one radio frequency (RF) power source to power multiple devices. The devices may include, for example: an RF defroster (e.g., to enable rapid defrosting from cold temperatures), an ultraviolet (UV) light source (e.g., to limit the growth of bacteria), and a plasma source (e.g., to break down organic compounds in the air to slow the aging of food and eliminate unpleasant odors). A controller adjusts the output of the RF power source to provide a frequency at which a selected device operates, and a switching arrangement directs the output of the RF source to the selected devices. The devices can thus provide multiple functions using common equipment. An apparatus for performing such functions (i.e., functions implemented using multiple devices) can be embodied as a standalone appliance, or can be incorporated into other systems (e.g., an appliance such as a refrigerator).

In some embodiments, one of the devices in the set of two or more devices may be a solid-state defroster that can be realized using a first electrode disposed in a cavity, an amplifier arrangement (including one or more transistors), an impedance matching network coupled between an output of the amplifier arrangement and the first electrode, and a measurement and control system that can detect when a defrosting operation has completed. In an embodiment, the impedance matching network is a variable impedance matching network that can be adjusted during the defrosting operation to improve matching between the amplifier arrangement and the cavity. As used herein, the term "defrosting" means a process by which the thermal energy or temperature of a load (e.g., a food load or other type of load) is increased through provision of RF power to the load. Accordingly, in various embodiments, a "defrosting operation" may be performed on a load with any initial temperature (e.g., any initial temperature below about 0 degrees Celsius), and the defrosting operation may be ceased at any final temperature that is higher than the initial temperature (e.g., including final temperatures that are above or below 0 degrees Celsius).

Another potential device in the set may be a plasma source capable of generating plasma. In certain embodiments, the plasma may be generated using, for example, a capacitively coupled plasma (CCP) source. A CCP source may include metallic electrodes separated by a small distance, with one electrode connected to the RF power supply, and the other electrode grounded. When an electric field is generated between the electrodes, atoms are ionized and release electrons. The electrons in the gas are accelerated by the RF field and can ionize the gas directly or indirectly by collisions, producing secondary electrons. When the electric field is strong enough, it can lead to what is known as electron avalanche. After avalanche breakdown, the gas becomes electrically conductive due to abundant free electrons.

A third potential device in the set may be a gas-discharge lamp that generates light by exciting plasma using RF power. In such lamps, a waveguide may be used to constrain and focus an electrical field into the plasma. Free electrons accelerated by the electrical field collide with gas and metal atoms. Electrons in the gas and metal atoms are excited by these collisions, bringing the electrons to a higher energy state. Materials in the plasma lamp are selected such that when the electrons fall back to their original (lower-energy) state, UV radiation is emitted.

Different combinations of devices can be incorporated in an appliance to achieve desired results depending on the specific application. For example, in certain embodiments, incorporating a UV source and a plasma source with a common RF power source can be useful for air purification/cleaning, as UV light inhibits growth of microorganisms like bacteria, and plasma reduces unpleasant odors by breaking down odor-causing molecules. Such an air purification system may purify air in, for example, a house, an office building, a health care facility (such as a hospital or clinic), a vehicle (personal or commercial), etc. In other embodiments, a plasma source and a defroster (with an RF power source) may be incorporated into an appliance. This pairing of devices may be useful in, for example, a refrigerator, allowing a user to defrost foods using the defroster, and to slow aging of food and reduce odors that may result from the defrost process by using plasma to break down organic molecules. In yet other embodiments, a UV source may additionally be incorporated in, for example, a refrigerator (or standalone appliance) that includes a defroster and plasma source sharing an RF power source, so as to provide anti-microbial functionality through irradiation with UV light.

FIG. 1 is a perspective view of a refrigerator/freezer appliance 100 in which two or more devices sharing an RF power generator may be incorporated. More specifically, a multifunctional system 110 is shown to be incorporated within a freezer compartment 112 of the system 100, and multifunctional system 120 is shown to be incorporated within a refrigerator compartment 122 of the system 100. An actual refrigerator/freezer appliance likely would include only one of the multifunctional systems 110, 120, but both are shown in FIG. 1 to concisely convey both embodiments. Each of multifunctional systems 110, 120 includes a heating cavity (inside of compartment 112, 122, respectively), and a control panel 114, 124. For example, the cavity may be defined by interior surfaces of bottom, side, front, and back walls of a drawer, and an interior top surface of a fixed shelf 116, 126 under which the drawer slides. With the drawer slid fully under the shelf, the drawer and shelf define the cavity as an enclosed air cavity. As used herein, the term "air cavity" may mean an enclosed area that contains air or other gases.

In the case of multifunctional systems with defrosters, a first electrode (e.g., electrode 270, FIG. 2) may be arranged proximate to a cavity wall, with the first electrode electrically isolated from the remaining cavity walls, and with the remaining cavity walls grounded. In other system implementations, multiple electrodes may be incorporated into a defrosting system in which an electric potential is established across the multiple electrodes to warm a food load therein. In such a configuration, the defroster may be simplistically modeled as a capacitor, where the first electrode functions as one conductive plate, the grounded cavity walls function as a second conductive plate (or electrode), and the air cavity (including any load contained therein) function as a dielectric medium between the first and second conductive plates. According to an embodiment, during operation of the multifunctional system 100, a user (not illustrated) may place one or more loads (e.g., food and/or liquids) into the defrosting cavity, and optionally may provide inputs via the control panel 114, 124 that specify characteristics of the load(s), such as an approximate weight or material of the load. In addition, the specified load characteristics may indicate the material(s) from which the load is formed (e.g., meat, bread, liquid). In alternate embodiments, the load characteristics may be obtained in some other way, such as by scanning a barcode on the load packaging or receiving a radio frequency identification (RFID) signal from an RFID tag on or embedded within the load. Either way, information regarding such load characteristics enables a system controller (e.g., system controller 230, FIG. 2) to establish an initial state for the impedance matching network of the system at the beginning of the defrosting operation, where the initial state may be relatively close to an optimal state that enables maximum RF power transfer into the load. Alternatively, load characteristics may not be entered or received prior to commencement of a defrosting operation, and the system controller may establish a default initial state for the impedance matching network.

The system controller causes the RF signal source(s) (e.g., RF signal source 240, FIG. 2) to supply an RF signal to the first electrode, which responsively radiates electromagnetic energy into a defrosting cavity of a multifunctional system 110, 120. The electromagnetic energy increases the thermal energy of the load (i.e., the electromagnetic energy causes the load to warm up). During the defrosting operation, the impedance of the load (and thus the total input impedance of the cavity plus load) changes as the thermal energy of the load increases. The impedance changes alter the absorption of RF energy into the load, and thus alter the magnitude of reflected power. According to an embodiment, power detection circuitry (e.g., power detection circuitry 278, FIG. 2) continuously or periodically measures the forward and/or reflected power along a transmission path (e.g., transmission path 248, FIG. 2) between the RF signal source (e.g., RF signal source 240, FIG. 2) and the first electrode. Based on these measurements, the system controller (e.g., system controller 230, FIG. 2) may detect completion of the defrosting operation. According to a further embodiment, the impedance matching network is variable, and based on the forward and/or reflected power measurements, the system controller may alter the state of the impedance matching network during the defrosting operation to increase the absorption of RF power by the load.

Those of skill in the art would understand, based on the description herein, that embodiments of defrosting systems may be incorporated into multifunctional systems or appliances having other configurations, as well. Accordingly, the above-described implementations of multifunctional systems in a stand-alone appliance, a freezer, and a refrigerator are not meant to limit use of the embodiments only to those types of systems. Although multifunctional systems 110, 120 are shown with their components in particular relative orientations with respect to one another, it should be understood that the various components may be oriented differently, as well. In addition, the physical configurations of the various components may be different. For example, control panels 114, 124 may have more, fewer, or different user interface elements, and/or the user interface elements may be differently arranged. In addition, although a substantially cubic cavity is indicated in FIG. 1, it should be understood that a defrosting cavity may have a different shape, in other embodiments (e.g., cylindrical, and so on). Further, defrosting systems within the multifunctional systems 110, 120 may include additional components (e.g., a fan, a stationary or rotating plate, a tray, an electrical cord, and so on) that are not specifically depicted in FIG. 1 or elsewhere in the drawings.

Figure 2:
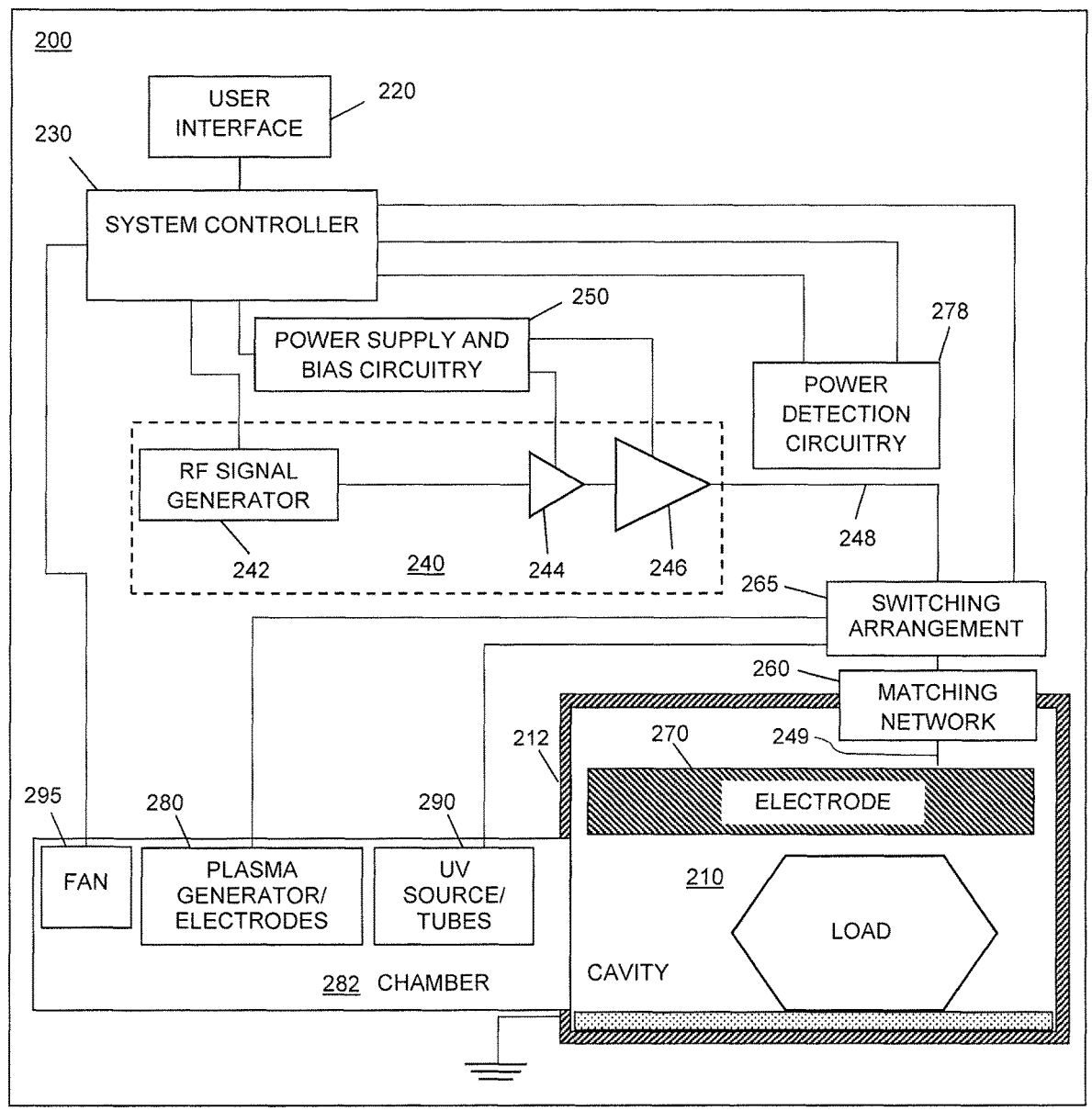
FIG. 2 is a simplified block diagram of a multifunctional RF system, in accordance with an example embodiment.

Various multifunctional system embodiments incorporate devices which may (or may not) be co-located with each other. FIG. 2 is a simplified block diagram of a multifunctional system 200 (e.g., multifunctional system 110, 120, FIG. 1), in accordance with an example embodiment. Multifunctional system 200 includes defrosting cavity 210, user interface 220, system controller 230, RF signal source 240, power supply and bias circuitry 250, variable impedance matching network 260, electrode 270, and power detection circuitry 278, in an embodiment. In addition, in other embodiments, multifunctional system 200 may include a plasma electrode used as part of a plasma generator 280 in an air purification chamber 282. Multifunctional system 200 may also include one or more UV tubes used as part of a UV source 290, which may also be located in the air purification chamber 282 in certain embodiments, or may be located within a separate chamber (not pictured). In various embodiments, UV source 290 may include a filament disposed with a transparent (e.g., glass) tube. Such a UV source 290 may be electrodeless and so may not incorporate metal contacts at either end of the transparent tube. According to an embodiment, one or more open or baffled openings may be present between the defrosting cavity 210 and the air purification chamber 282 so that air may be exchanged between the cavity 210 and the chamber 282. In other embodiments, the system may be configured so that the air purification chamber 282 also or alternatively may exchange air with other system spaces (e.g., the interiors of a refrigerator and/or freezer compartment 112, 122).

In certain embodiments, one or more fans 295 are located in (or are otherwise in fluid communication with) the air purification chamber 282 and/or the cavity 210. The fan 295 may be used to circulate air to effect air exchange between the air purification chamber/cavity and the surrounding ambient air (e.g., air in the interior refrigerator and/or freezer compartments 112, 122). For example, plasma may be generated using plasma electrodes of a plasma generator 280, and UV light may be emitted using UV tubes of a UV source 290, for application of plasma and UV light to air in the air purification chamber 282. In an embodiment, plasma generator 280 and UV source 290 may share the same housing. The fan 295 may then exchange the air treated with plasma and/or UV light in the air purification chamber with, for example, air outside of the air purification chamber 282, such as air in the cavity 210 or air in the appliance (stand-alone or otherwise) that includes multifunctional system 200. In various embodiments, the fan 295 may be controlled by the system controller 230 (such that the fan 295 is turned on, or its speed varied, by the system controller 230 based on, for example, the timing of plasma generation and/or UV light irradiation). In other embodiments, the fan 295 may be controlled by (independently or in conjunction with) a controller of an appliance into which the multifunctional system 200 is incorporated. For example, a controller of a refrigerator may run the fan 295 according to a schedule that may be independent of, or coordinated with, a schedule for application of plasma and/or UV light.

It should be understood that FIG. 2 is a simplified representation of a multifunctional system 200 for purposes of explanation and ease of description, and that practical embodiments may include other devices and components to provide additional functions and features, and/or the multifunctional system 200 may be part of a larger electrical system. In other embodiments, for example, multifunctional system 200 may have a plasma generator 280 (e.g., plasma generator 280, FIG. 2) and UV source 290 (e.g., UV source 290, FIG. 2), but no defroster. Alternatively, in some embodiments, the multifunctional system 200 may include a defroster with either a plasma generator or a UV source (but not both).

User interface 220 may correspond to a control panel (e.g., control panel 114, 124, FIG. 1), for example, which enables a user to provide inputs to the system regarding parameters for a defrosting operation (e.g., characteristics of the load to be defrosted, and so on), a plasma generation operation (e.g., duration and timing of plasma generation), a UV source operation (e.g., timing and intensity of UV light), start and cancel buttons, mechanical controls (e.g., a door/drawer open latch), and so on. In addition, the user interface 220 may be configured to provide user-perceptible outputs indicating the status of a defrosting operation (e.g., a count-down timer, visible indicia indicating progress or completion of the defrosting operation, and/or audible tones indicating completion of the defrosting operation) and other information.

System controller 230 may include one or more general purpose or special purpose processors (e.g., a microprocessor, microcontroller, Application Specific Integrated Circuit (ASIC), and so on), volatile and/or non-volatile memory (e.g., Random Access Memory (RAM), Read Only Memory (ROM), flash, various registers, and so on), one or more communication busses, and other components. According to an embodiment, system controller 230 is coupled to user interface 220, RF signal source 240, variable impedance matching network 260, power detection circuitry 278, plasma generator 280, UV source 290, and fan 295. System controller 230 is configured to receive signals indicating user inputs received via user interface 220, and to receive forward and/or reflected power measurements from power detection circuitry 278. Responsive to the received signals and measurements, system controller 230 provides control signals to the power supply and bias circuitry 250 and to the RF signal generator 242 of the RF signal source 240. In addition, system controller 230 provides control signals to the variable impedance matching network 260, which causes the matching network 260 to change its state or configuration.

A switching arrangement 265 is configured to selectively connect the output of RF signal source 240 to the defroster (e.g., to electrode 270), the plasma generator 280 (e.g., plasma generator 280 including plasma electrodes), and the UV source 290 (e.g., UV source 290 including UV tubes). The devices powered using RF signal source 240 may require certain frequencies (i.e., be designed to operate using RF signals with frequencies falling in different frequency bands), and the system controller 230 may direct the RF signal generator 242 to generate RF signals with frequencies suited to the device being powered using the RF signal source 240. The switching arrangement 260 may be instructed to switch to another device as specified by the system controller 230. In other embodiments, if the devices are operated at different frequencies (e.g., within non-overlapping frequency bands), the switching arrangement may detect the RF frequency being provided by the RF signal source 240 (as directed by system controller 230) and switch to the device which operates at that corresponding frequency. When switching the RF signal source 240 between devices (e.g., UV source 240, plasma generator 208, and electrode 270), the RF signal source 240 may be configured to reduce a power of an RF signal outputted by RF signal source 240 which may, in turn, reduce the likelihood of potential damage to the switching arrangement as well as reducing the creation of transient signal at the time of switching. After the switching arrangement has connected the desired device (e.g., plasma generator 208, UV source 240, or electrode 270) to the RF signal source 240, the power of the signal outputted by RF signal source 240 can against be increased.

The first electrode 270 is electrically coupled to the RF signal source 240 through a variable impedance matching network 260 and a transmission path 248, in an embodiment. The variable impedance matching circuit 260 is configured to perform an impedance transformation from an impedance of the RF signal source 240 to an input impedance of defrosting cavity 210 as modified by a load in the cavity 210. In an embodiment, the variable impedance matching network 260 includes a network of passive components (e.g., inductors, capacitors, resistors). According to a more specific embodiment, the variable impedance matching network 260 includes a plurality of fixed-value lumped inductors that are positioned within the cavity 210 and which are electrically coupled to the first electrode 270. In addition, the variable impedance matching network 260 includes a plurality of variable inductance networks, which may be located inside or outside of the cavity 210. The inductance value provided by each of the variable inductance networks is established using control signals from the system controller 230. In any event, by changing the state of the variable impedance matching network 260 over the course of a defrosting operation to dynamically match the ever-changing cavity input impedance, the amount of RF power that is absorbed by the load may be maintained at a high level despite variations in the load impedance during the defrosting operation.

System 200 also provides impedance matching for the plasma electrodes of the plasma generator 280 and UV tubes of the UV source 290, but the input impedances of these devices do not necessarily fluctuate in the same way as the defroster (which includes a load with an impedance that may change significantly as it is heated). For devices with input impedances that are relatively stable over time, a variable impedance matching network may not be necessary. For example, the input impedances of the plasma electrodes of the plasma generator 280 and UV tubes of the UV source 290 may stay fairly static over time. Consequently, an impedance of the RF signal source 240 is matched to an impedance of the plasma electrodes or the UV tubes when one of the corresponding devices is to be operated.

According to an embodiment, RF signal source 240 includes an RF signal generator 242 and a power amplifier (e.g., including one or more power amplifier stages 244, 246). In response to control signals provided by system controller 230, RF signal generator 242 is configured to produce an oscillating electrical signal having a desired frequency. The RF signal generator 242 may be controlled to produce oscillating signals of different power levels and/or different frequencies, in various embodiments. For example, the RF signal generator 242 may produce a signal that oscillates in a range of about 3.0 megahertz (MHz) to about 300 MHz. Some desirable frequencies may be, for example, 13.56 MHz (+/−5 percent), 27.125 MHz (+/−5 percent), and 40.68 MHz (+/−5 percent). In an embodiment, the plasma generator, for example, may be driven by an RF signal, produced by the RF signal generator 342, with a frequency of about 13.56 MHz, and a power level in a range of about 1 W to 5 kW, though in some embodiments the power level may be in the range of 1-20 W. In another embodiment, for example, the RF signal generator 342 may produce a signal that oscillates in a range of about 40.66 MHz to about 40.70 MHz and at a power level in a range of about 1 W to 5 kW for use by the defroster. In yet another embodiment, for example the RF signal generator 342 may be controlled to produce a signal with a power level in a range of about 1 W to about 20 W or higher for use by the UV tubes of UV source 290. Alternatively, the frequencies of oscillation and/or the power levels may be lower or higher. For example, when supplying a signal to only UV source and plasma generator the RF signal generator 342 may provide a signal having a frequency that ranges from 1 MHz up to 10 gigahertz (GHz). When supplying a signal to the UV source, plasma generator, and the heating electrode, for example, the RF signal generator 342 may provide a signal having a frequency that ranges from 1 MHz up to 1 GHz, for example. Either way, the above examples indicate that the RF signal generator 342 and the amplifier stages 244, 246 may be controlled (e.g., by system controller 230) to provide an RF signal to the switching arrangement 265 that may have a different frequency and/or different power level depending on whether the switching arrangement 265 is providing the signal to the defroster, to the plasma generator 280 or to the UV source 290.

In the embodiment of FIG. 2, the power amplifier includes a driver amplifier stage 244 and a final amplifier stage 246. The power amplifier is configured to receive the oscillating signal from the RF signal generator 242, and to amplify the signal to produce a significantly higher-power signal at an output of the power amplifier. For example, the output signal may have a power level in a range of about 100 watts to about 400 watts or more, although the output signal may have a lower power level, as well. The gain applied by the power amplifier may be controlled using gate bias voltages and/or drain supply voltages provided by the power supply and bias circuitry 250 to each amplifier stage 244, 246. More specifically, power supply and bias circuitry 250 provides bias and supply voltages to each RF amplifier stage 244, 246 in accordance with control signals received from system controller 230.

In an embodiment, each amplifier stage 244, 246 is implemented as a power transistor, such as a field effect transistor (FET), having an input terminal (e.g., a gate or control terminal) and two current carrying terminals (e.g., source and drain terminals). Impedance matching circuits (not illustrated) may be coupled to the input (e.g., gate) of the driver amplifier stage 244, between the driver and final amplifier stages 246, and/or to the output (e.g., drain terminal) of the final amplifier stage 246, in various embodiments. In an embodiment, each transistor of the amplifier stages 244, 246 includes a laterally diffused metal oxide semiconductor FET (LDMOSFET) transistor. However, it should be noted that the transistors are not intended to be limited to any particular semiconductor technology, and in other embodiments, each transistor may be realized as a gallium nitride (GaN) transistor, another type of MOSFET transistor, a bipolar junction transistor (BJT), or a transistor utilizing another semiconductor technology.

In FIG. 2, the power amplifier arrangement is depicted to include two amplifier stages 244, 246 coupled in a particular manner to other circuit components. In other embodiments, the power amplifier arrangement may include other amplifier topologies and/or the amplifier arrangement may include only one amplifier stage, or more than two amplifier stages. For example, the power amplifier arrangement may include various embodiments of a single ended amplifier, a double ended amplifier, a push-pull amplifier, a Doherty amplifier, a Switch Mode Power Amplifier (SMPA), or another type of amplifier.

Power detection circuitry 278 may be coupled along the transmission path 248 between the output of the RF signal source 240 and the input to the switching arrangement 265, in various embodiments. In an alternate embodiment, power detection circuitry 278 may be coupled to the transmission path 249 between the output of the matching network 260 and the first electrode 270. Either way, power detection circuitry 278 is configured to monitor, measure, or otherwise detect the power of the forward signals (i.e., from RF signal source 240 toward first electrode 270) and/or the reflected signals (i.e., from first electrode 270 toward RF signal source 240) traveling along the transmission path 248.

Power detection circuitry 278 supplies signals conveying the magnitudes of the forward and reflected signal power to system controller 230. System controller 230, in turn, may calculate a ratio of reflected signal power to forward signal power, or the S11 parameter. When the reflected power exceeds a threshold or the reflected to forward power ratio exceeds a threshold, this indicates that the system 200 is not adequately matched, and that energy absorption by the load may be sub-optimal. In such a situation, system controller 230 orchestrates a process of altering the state of the variable impedance matching network until the reflected power or the reflected to forward power ratio decreases to a desired level, thus re-establishing an acceptable match and facilitating more optimal energy absorption by the load.

Some embodiments of multifunctional system 200 may include temperature sensor(s), IR sensor(s), and/or weight sensor(s) to provide data to the system controller 230. Information from the sensors (e.g., temperature information) enables the system controller 230 to alter the power of the RF signal supplied by the RF signal source 240 (e.g., by controlling the bias and/or supply voltages provided by the power supply and bias circuitry 250), to adjust the state of the variable impedance matching network 260, and/or to determine when the operations (e.g., defrosting) should be terminated. The weight sensor(s) may be positioned under the load, and are configured to provide an estimate of the weight of the load to the system controller 230, which may use the weight information, for example, to determine a desired power level for the RF signal supplied by the RF signal source 240, to determine an initial setting for the variable impedance matching network 260, and/or to determine an approximate duration for the defrosting operation.

According to an embodiment, the variable impedance matching network 260 may include a network of passive components, and more specifically a network of fixed-value inductors (e.g., lumped inductive components) and variable inductors (or variable inductance networks). As used herein, the term "inductor" means a discrete inductor or a set of inductive components that are electrically coupled together without intervening components of other types (e.g., resistors or capacitors).

Figure 3:
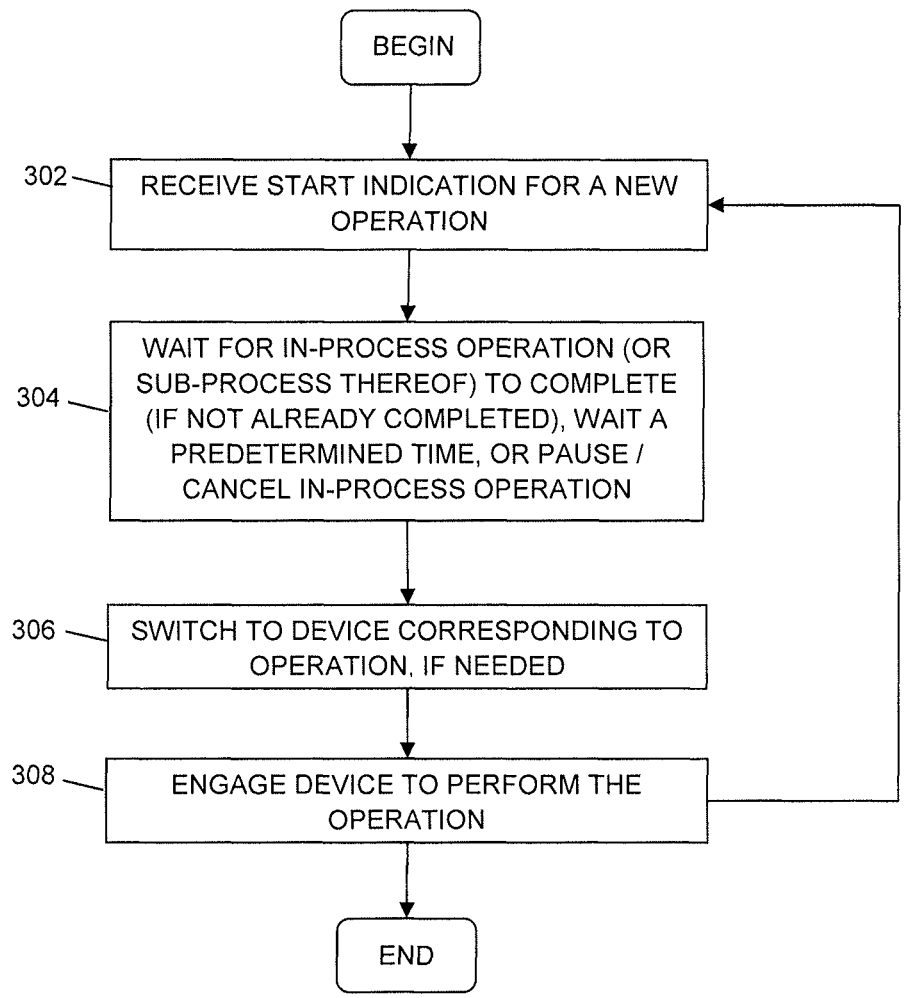
FIG. 3 is a flowchart of a method of operating a multifunctional RF system, in accordance with an example embodiment.

Various embodiments of methods for operating such multifunctional systems will now be described in conjunction with FIG. 3. More specifically, FIG. 3 is a flowchart of a method of operating a multifunctional system (e.g., system 200, FIG. 2), in accordance with an example embodiment. The method may begin, in block 302, when the system controller (e.g., system controller 230, FIG. 2) receives an indication that a new operation (e.g., defrosting, plasma generation, or UV irradiation) should start. Such an indication may be received, for example, after a user has placed a load into a defrosting cavity (e.g., cavity 210, FIG. 2), has sealed the cavity (e.g., by closing a door or drawer), and has pressed a start button (e.g., of the user interface 220, FIG. 2). Such an indication may also be based on a predetermined schedule provided to, or saved by, the system controller, such as generation of plasma or UV light at certain times or with a certain frequency (e.g., at midnight, once per hour, etc.). Alternatively, such an indication may also be based on the occurrence of another triggering event, such as the completion of a defrosting operation, an air quality measurement within the cavity crossing a threshold, a temperature of the cavity crossing a threshold, the opening or closing of a door or drawer, and so on.

In block 304, if an operation is currently being performed by a device (i.e., if an operation is "in-process"), the system controller may wait for the in-process operation to complete. For example, if the in-process operation is defrosting a load, the system controller may wait for the defrost operation to complete. Alternatively, the system controller may wait for a sub-process of the in-process operation to complete. For example, if a defrost operation involves alternating between the sub-processes of energizing an electrode for a time (e.g., five minutes) and pausing energizing the electrode for a time (e.g., five minutes), the system controller may wait for a pause between repeating energizations (e.g., the system controller may wait for one sub-process to complete). In other embodiments, the system controller may wait a predetermined/preset time (e.g., one minute) to allow an in-process operation (such as UV irradiation) to continue for a time before it is stopped. In other embodiments, the system controller may pause an in-process operation, then resume the paused operation after the new operation is completed. Alternatively, the system controller may alternate between the paused operation and the new operation. In yet other embodiments, an in-process operation may be canceled if a new operation is to be performed. The canceled operation may be performed later according to a new user command, preset schedule, or triggering event.

In block 306, if the new operation is to be performed using a device not already selected for being powered by the RF power generator (i.e., the switching arrangement is not already configured to provide the RF signal to the device), the system controller (e.g., system controller 230) may provide a control signal to cause the switching arrangement (e.g., switching arrangement 265) to change (switch) from an idle state or from providing the RF signal generated by the RF signal source (e.g., RF signal source 240) to a device used to perform a previous/in-process operation, to providing the RF signal to another (new) device to be used to perform the new operation. This may involve adjusting the RF frequency produced by the RF signal generator to an operational frequency for the new device, as needed. In block 308, the device now being powered by the RF power source (i.e., the device now being provided the RF signal) is engaged to perform the new operation. More specifically, one or more control signals may be provided to the new device to cause the device to convert or consume the RF signal, as appropriate, to excite the electrodes (e.g., electrode 270 or the electrode(s) of the plasma generator 280) or tubes (e.g., the UV tubes of the UV source 290) in order to perform the intended function of the device. The operation then continues until a start indication is received for a new operation (block 304), or until the operation completes (e.g., a timeout occurs, completion of the operation is detected, the operation is interrupted, or another event triggering operation cessation occurs). It should be understood that the order of operations associated with the blocks depicted in FIG. 3 corresponds to an example embodiment, and should not be construed to limit the sequence of operations only to the illustrated order. Instead, some operations may be performed in different orders, and/or some operations may be performed in parallel.

Figure 4:
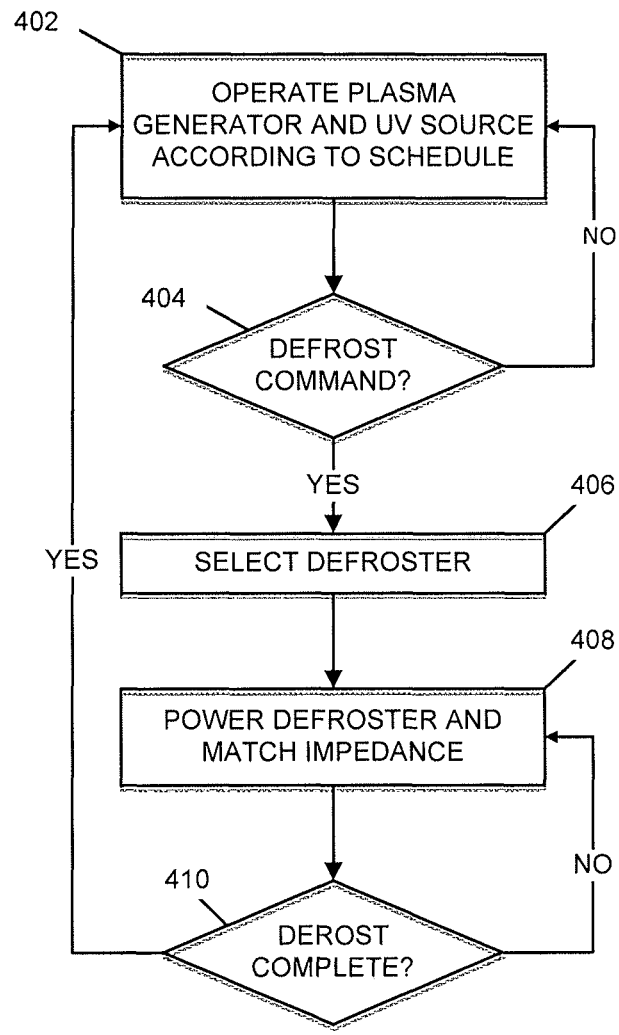
FIG. 4 is a flowchart of a method of operating a multifunctional RF system with a plasma generator, ultraviolet (UV) source, and defroster, in accordance with an example embodiment.

FIG. 4 is a flowchart of a method of operating a multifunctional system with a plasma generator (e.g., plasma generator 280), UV source (e.g., UV source 290), and defroster (e.g., including matching network 260 and electrode 270), in accordance with an example embodiment. In block 402, a controller of the multifunctional system (e.g., system controller 230) may send control signals to operate the plasma generator and UV source according to a predetermined schedule (which may be, e.g., factory preset, or programmed by a user). For example, the system controller may send control signals to the switching arrangement (e.g., switching arrangement 265) to provide an RF signal to the plasma generator (and to the plasma electrodes), and control signals to the plasma generator to generate plasma for a period of time (e.g., one minute each hour, or some other time period based on a triggering event). At different times, the system controller may send control signals to the switching arrangement to provide an RF signal to the UV source (and to the UV tubes), and control signals to the UV source to generate UV light for a period of time (e.g., five minutes each hour, or some other time period based on a triggering event). The system controller may schedule a break between plasma and UV operations. Each time the plasma generator is to be activated, the frequency and impedance of the RF signal source (e.g., RF signal source 240) are adjusted to correspond with the operational frequency and impedance of the plasma generator, and the switching arrangement connects the output of the RF signal source to the plasma generator, in certain embodiments. Similarly, each time the UV source is to be activated, the frequency and impedance of the RF signal source are adjusted to correspond with the operational frequency and impedance of the UV source, and the switching arrangement connects the output of the RF signal source to the UV source, in certain embodiments. In other embodiments, one or both of the plasma generator and UV source may alternatively or additionally also be operated upon a user command (received via a user interface) or based on another triggering event. Further, although an embodiment includes operating the plasma generator and UV source during non-overlapping time periods, other embodiments may include simultaneous operation of the plasma generator and UV source.

In block 404, the system controller determines whether a command to initiate a defrost operation is received (e.g., from a user through the user interface, or as a result of a prescheduled defrost operation). This determination may be performed repeatedly between plasma and UV generation operations, in certain embodiments, or may be made based on an interrupt. In other embodiments, the check may be performed more frequently (e.g., during plasma and UV generation operations, in which case the plasma/UV operation may be, e.g., paused or canceled, as discussed above), or less frequently (e.g., once every 20 seconds on a periodic basis, or once every 20 seconds only between plasma and UV generation operations). If no defrost initiation command is received (404), the system controller continues with its scheduled plasma and UV generation operations (402). When a defrost command is received (404), then in block 406, the system controller causes the switching arrangement to connect the defroster (e.g., matching network 260 and electrode 270) to the output of the RF signal source (e.g., RF signal source 240). In block 408, the RF signal source is used to power the defroster, and a variable impedance matching network (e.g., matching network 260) is used to match RF signal source and defroster impedances, as discussed above. In block 410, when the defrost operation has completed (which may be determined based on a temperature and/or impedance of the load, for example), the system controller may return to providing control signals to perform the plasma and UV generation operations (402). When the defrost operation has not completed, the RF signal source continues to power the defroster, and the variable impedance matching network continues to match impedances until the defrost operation is completed.

In alternative embodiments, the defrost operation may be interrupted (paused) to allow, for example, scheduled plasma and/or UV operations to be performed. In such embodiments, when a defrost operation is to be paused for a plasma operation, the plasma generator is powered until the plasma operation is completed; similarly, when a defrost operation is to be paused for a UV operation, the UV generator is powered until the UV operation is completed. Once the plasma/UV operation has been performed, the defroster may be powered to resume the defrosting operation.

Figure 5:
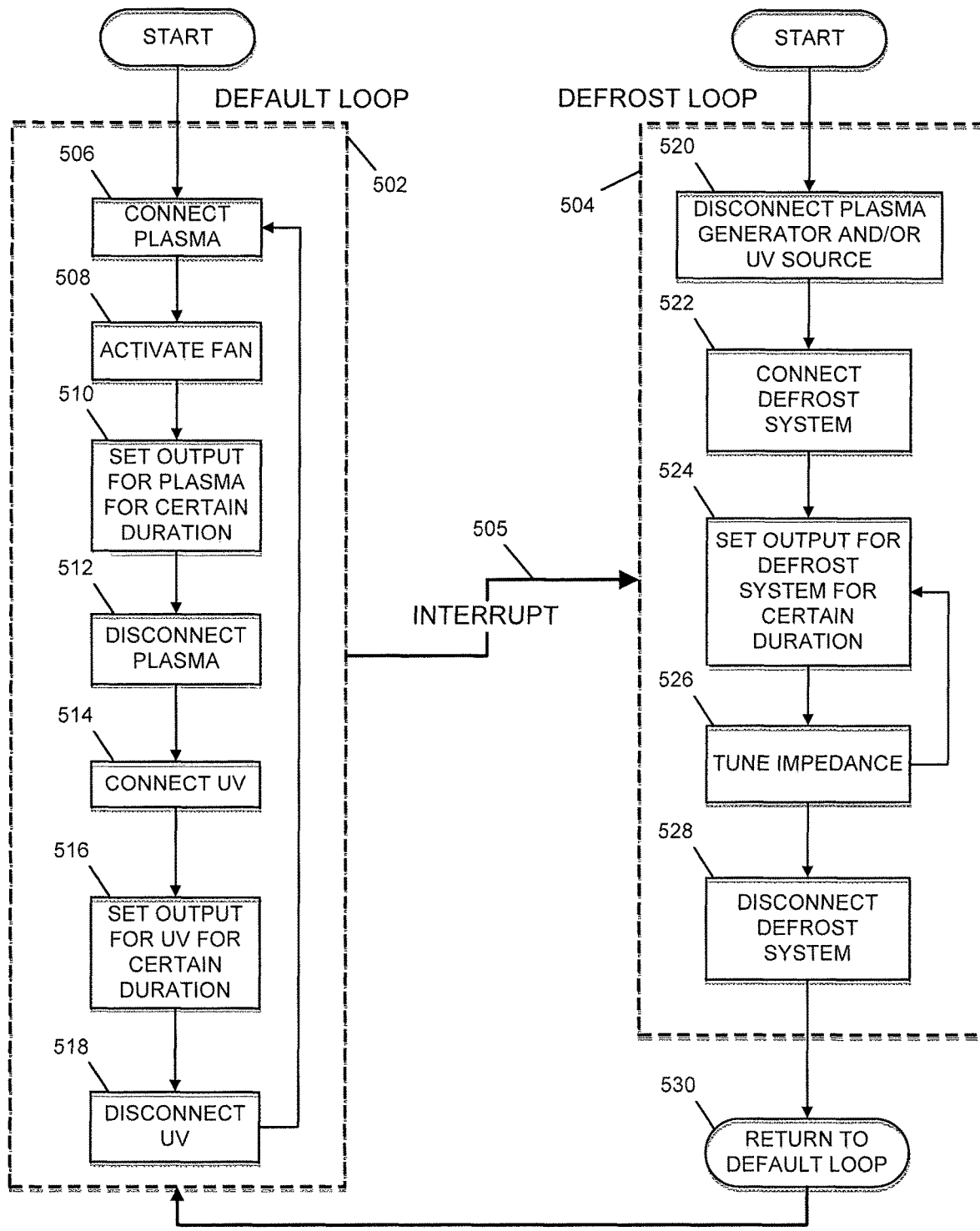
FIG. 5 is a flowchart of a method of operating a multifunctional RF system with a plasma generator, UV source, and defroster, in accordance with another example embodiment.

FIG. 5 is a flowchart of a method of operating a multifunctional system with a plasma generator, UV source, and defrost system, in accordance with another example embodiment. The method involves a default loop (502) and a defrost/cooking loop (504). The default loop (502) involves using a plasma generator and UV source to purify air according to a predetermined schedule, until air purification is interrupted (505) by a preset schedule or user command for a defrost operation, at which time the defrost/cooking loop (504) is executed until the defrost operation has completed, is interrupted, or has otherwise run its course.

In block 506, the system controller sends control signals to the switching arrangement to connect the plasma generator to the RF signal source. Next, in block 508, the system controller may send control signals to activate a fan (e.g., fan 295) so that air treated with the plasma can be circulated through an air purification chamber/appliance. In block 510, the system controller sends control signals to the RF signal source to set the output signal produced by the RF signal source to a frequency required by the plasma generator. The RF signal source provides an RF signal to the plasma generator for a certain period of time (according to a preset schedule) until, in block 512, the system controller sends control signals to the switching arrangement to disconnect the plasma generator from the RF signal source. In block 514, the system controller sends control signals to the switching arrangement to connect the UV source to the RF signal source and, in block 516, the system controller sends additional control signals to the RF signal source to set the output signal produced by the RF signal source to a frequency required by the UV source. The system controller may cause the RF signal source to provide an RF signal to the UV source for a certain period of time (according to a preset schedule) until, in block 518, the system controller sends control signals to the switching arrangement to disconnect the UV source from the RF signal source. The default loop process then repeats by looping back to block 506, allowing the system controller again to operate the plasma generator based on the preset schedule. It is noted that the default loop (502) may alternatively begin by connecting the UV source to the RF signal source, or by activating the fan, instead of connecting the plasma generator to the RF power source. In other words, the order of operations in the default loop may be different from that depicted in FIG. 5.

When an interrupt (505) occurs (e.g., a user command is received to perform a defrost operation, or the time for a scheduled defrost operation is reached), the plasma generator or the UV source may be connected to the RF signal source, although the corresponding operation may or may not be executing, as the system controller may be waiting for a next scheduled plasma/UV operation time to arrive according to a predetermined schedule. When the plasma operation or the UV operation currently is running, the system controller may send control signals to halt operations of the plasma generator or UV source, and to cause the switching arrangement to disconnect the plasma generator or UV source from the RF signal source. Alternatively, in some embodiments, the system controller may wait for the currently executing plasma/UV operation to complete its current operation. In other embodiments, the system controller may allow the in-process operation to complete only when the remaining time to completion is below a certain minimum time threshold. For example, when there is no more than one minute (or some other time period) remaining in a plasma or UV operation, the system controller may allow the operation to be completed before beginning a defrost operation. In yet other embodiments, the system controller may continue executing the in-process operation for an additional preset duration, such as 30 seconds (or some other time period), regardless of whether the operation would be completed after the preset duration. Alternatively, the system controller may stop the in-process operation only when the operation has been running for a certain minimum time (such as 30 seconds or some other period), so that a device is not stopped immediately (or shortly) after starting. This may be useful, for example, in case the device would experience excessive wear-and-tear from rapid transitions (power-ups and power-downs).

The interrupt (505) from default loop (502) to defrost/cooking loop (504) may feed certain information related to the defrost/cooking operation to the system controller. This information may be based on, for example, entries input by a user through a user interface, and/or calculations made by the system controller. Such information may include the duration of a defrost or cooking operation, the type of food, the quantity of food, and so on. The defrost/cooking loop (504) begins, in block 520, by the controller sending control signals to the switching arrangement to disconnect the plasma generator or UV source, whichever is connected. The system controller may then, in block 522, send control signals to the switching arrangement to connect the defroster to the RF signal source, and in block 524, to set the output signal produced by the RF signal source to a frequency required by the defroster. The system controller may additionally set a defrost operation duration, which may have been input by the user or calculated based on the type and quantify of food. The system controller may, in block 526, send control signals to tune the impedance as the defrost operation proceeds using the variable impedance matching network (e.g., matching network 260), as discussed above. Once the defrost operation has completed or otherwise has been interrupted, the system controller, in block 528, sends control signals to the switching arrangement to disconnect the defrost system from the RF signal source and, in block 530, the process returns to the default loop (502).

As discussed, embodiments of a multifunctional system include an RF excitation signal source configured to produce an RF excitation signal, and a switching system or arrangement configured to provide the RF excitation signal to one of multiple devices. The system may be embodied in a standalone appliance, or may be incorporated into a larger system, such as commercial and industrial appliances (e.g., countertop and refrigerator-type appliances that incorporate a hybrid defrost/air purification/sterilization system). In certain embodiments, the multifunctional system may include components of a defrost system (e.g., a matching network, an electrode, a grounded housing, and so on), a UV source (including UV tubes), and a plasma generator (including plasma electrodes), all selectively coupled to a common RF signal source. The system also may include a switching arrangement, which enables an RF signal to be provided to the defrost components (when a defrost operation is underway), to the UV source (when UV sterilization of the load is desired), or to the plasma generator (when air sterilization is desired). For the sterilization processes, air from a cavity may be circulated through a separate purification chamber. The multifunctional system can instead, in other embodiments, incorporate any set of devices to be powered by an RF signal source.

The connecting lines shown in the various figures contained herein are intended to represent exemplary functional relationships and/or physical couplings between the various elements. It should be noted that many alternative or additional functional relationships or physical connections may be present in an embodiment of the subject matter. In addition, certain terminology may also be used herein for the purpose of reference only, and thus are not intended to be limiting, and the terms "first", "second" and other such numerical terms referring to structures do not imply a sequence or order unless clearly indicated by the context.

The foregoing description refers to elements or nodes or features being "connected" or "coupled" together. As used herein, unless expressly stated otherwise, "connected" means that one element is directly joined to (or directly communicates with) another element, and not necessarily mechanically. Likewise, unless expressly stated otherwise, "coupled" means that one element is directly or indirectly joined to (or directly or indirectly communicates with) another element, and not necessarily mechanically. Thus, although the schematic shown in the figures depict one exemplary arrangement of elements, additional intervening elements, devices, features, or components may be present in an embodiment of the depicted subject matter.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

EXAMPLES

Illustrative examples of the technologies disclosed herein are provided below. An embodiment of the technologies may include any one or more, and any combination of, the examples described below.

In an example embodiment, a system comprises: a housing including a first cavity configured to contain a load; a defrost system at least partially disposed in the first cavity, the defrost system being configured to receive a first radio frequency (RF) signal at a first frequency to defrost the load within the first cavity; a first air treatment device in fluid communication with the housing, the first air treatment device being configured to receive a second RF signal at a second frequency, and to perform an air treatment process in response to the second RF signal; an RF signal source having a power output for outputting RF signals; a switching arrangement configured to selectively electrically connect the defrost system and the first air treatment device to the power output of the RF signal source; and a controller configured to: cause the switching arrangement to electrically connect one of the defrost system and the first air treatment device to the power output of the RF signal source, when the defrost system is electrically connected to the power output of the RF signal source, cause the RF signal source to output the first RF signal at the first frequency, and when the first air treatment device is electrically connected to the power output of the RF signal source, cause the RF signal source to output the second RF signal at the second frequency.

According to a further example embodiment, the system further comprises: a second air treatment device in fluid communication with the housing, the second air treatment device being configured to receive a third RF signal at a third frequency, and to perform an air treatment process in response to the third RF signal, and wherein the controller is further configured to cause the switching arrangement to electrically connect the second air treatment device to the power output of the RF signal source.

According to a further example embodiment of the system, the first and second air treatment devices are selected from a plasma generator and an ultraviolet source.

According to a further example embodiment, the system further comprises a variable impedance network having a first terminal coupled to the switching arrangement and a second terminal coupled to the defrost system.

According to a further example embodiment of the system, the controller is configured to adjust an impedance of the variable impedance network to match an impedance of the RF signal source to an impedance of the defrost system.

According to a further example embodiment of the system, the controller is configured to cause the switching arrangement to electrically connect the first air treatment device, and the second air treatment device to the power output of the RF signal source according to a predetermined schedule.

According to a further example embodiment, the system further comprises a user interface configured to transmit a control signal to the controller in response to a user input, wherein the controller is configured to cause the switching arrangement to electrically connect one of the defrost system and the first air treatment device to the power output of the RF power source in response to the control signal.

According to a further example embodiment, the system further comprises an air purification chamber in fluid communication with the housing and wherein the first air treatment device is disposed within the air purification chamber.

According to a further example embodiment, the system further comprises a fan disposed within the air purification chamber, the fan being connected to the controller and the controller being configured to activate the fan when the second RF signal at the second frequency is supplied to the first air treatment device.

In another example embodiment, a multifunctional radio frequency (RF) appliance comprises: an RF signal source having a power output for supplying RF signals at multiple output frequencies; a first device configured to be powered by a first RF signal at a first frequency; a second device configured to be powered by a second RF signal at a second frequency; a switching arrangement configured to selectively electrically connect the first device and the second device to the power output of the RF signal source; and a controller configured to: cause the switching arrangement to electrically disconnect the first device from the power output of the RF signal source and electrically connect the second device to the power output of the RF signal source, determine the second frequency of the second RF signal, and cause the RF signal source to supply the second RF signal at the second frequency to the second device.

According to a further example embodiment, the multifunctional RF appliance further comprises a variable impedance network having a first terminal connected to the switching arrangement and a second terminal coupled to the second device.

According to a further example embodiment of the multifunctional RF appliance, the controller is configured to adjust an impedance of the variable impedance network to match an impedance of the RF power source to an impedance of the second device.

According to a further example embodiment of the multifunctional RF appliance, the controller is configured to cause the switching arrangement to electrically disconnect the first device from the power output of the RF signal source and electrically connect the second device to the power output of the RF signal source according to a predetermine schedule.

According to a further example embodiment, the multifunctional RF appliance further comprises a user interface configured to transmit a control signal to the controller in response to a user input and wherein the controller is configured to cause the switching arrangement to electrically disconnect the first device from the power output of the RF signal source and electrically connect the second device to the power output of the RF signal source in response to the control signal.

According to a further example embodiment of the multifunctional RF appliance, the second device is selected from a plasma generator and an ultraviolet source situated in an air purification chamber.

According to a further example embodiment, the multifunctional RF appliance further comprises a fan disposed within the air purification chamber, the fan being connected to the controller and the controller being configured to activate the fan when the second RF signal at the second frequency is supplied to the second device.

In yet another example embodiment, a method comprises electrically connecting one of a defrost system, a plasma generator, and an ultraviolet generator to a power output of a radio frequency (RF) signal source, wherein: the defrost system is configured to receive a first RF signal from the RF signal source to defrost a load; the plasma generator is configured to receive a second RF signal from the RF signal source to generate plasma; and the ultraviolet generator is configured to receive a third RF signal from the RF signal source to generate ultraviolet light; when the defrost system is electrically connected to the power output of the RF signal source, providing the defrost system with the first RF signal, when the plasma generator is electrically connected to the power output of the RF signal source, providing the plasma generator with the second RF signal, and when the ultraviolet generator is electrically connected to the power output of the RF signal source, providing the ultraviolet generator with the third RF signal.

According to a further example embodiment, the method further includes modifying an output impedance of the RF signal source based on an input impedance of the defrost system when the defrost system is being powered by the RF power source.

According to a further example embodiment, the method further includes: powering the plasma generator and the ultraviolet generator with the RF power source according to a predetermined schedule; and exchanging air treated with plasma generated by the plasma generator and ultraviolet light generated by the ultraviolet generator with air outside of an air purification chamber.

According to a further example embodiment, the method further includes powering the plasma generator and ultraviolet generator based on a preset schedule, and interrupting power to the plasma generator and the ultraviolet generator to power the defrost system upon receiving a user input or an interrupt.

What is claimed is:

1. A method comprising:
controlling, by a controller, a switching arrangement to electrically connect one of a defroster and a first air treatment device to a power output of a radio frequency (RF) signal source,
wherein the defroster is configured to radiate electromagnetic energy into a cavity configured to contain a load in response to receiving a first RF signal from the RF signal source, and
wherein the first air treatment device is configured to receive a second RF signal from the RF signal source, and to perform a first air treatment process in response to the second RF signal;
when the defroster is electrically connected to the power output of the RF signal source, providing the defroster with the first RF signal;
when the first air treatment device is electrically connected to the power output of the RF signal source, providing the first air treatment device with the second RF signal.

2. The method of claim 1, further comprising:
controlling the switching arrangement to electrically connect one of the defroster, the first air treatment device, and a second air treatment device to the power output of the RF signal source,
wherein the second air treatment device is configured to receive a third RF signal from the RF signal source, and to perform a second air treatment process in response to the third RF signal; and
when the second air treatment device is electrically connected to the power output of the RF signal source, providing the second air treatment device with the third RF signal.

3. The method of claim 1, further including modifying an output impedance of the RF signal source based on an input impedance of the defroster when the defroster is being powered by the RF power source.

4. The method of claim 1, wherein the first air treatment device is a plasma generator configured to generate plasma in response to the second RF signal.

5. The method of claim 4, further including:
powering the plasma generator with the RF signal source according to a predetermined schedule; and
exchanging air treated with plasma generated by the plasma generator with air outside of an air purification chamber.

6. The method of claim 1, wherein the first air treatment device is an ultraviolet generator configured to generate ultraviolet light in response to the second RF signal.

7. The method of claim 6, further including:
powering the ultraviolet generator with the RF signal source according to a predetermined schedule; and
exchanging air treated with ultraviolet light generated by the ultraviolet generator with air outside of an air purification chamber.

8. The method of claim 1, further comprising:
powering the first air treatment device based on a preset schedule, and interrupting power to the first air treatment device to power the defroster upon receiving a user input or an interrupt.

9. The method of claim 1, further comprising:
transmitting, by a user interface, a control signal to the controller in response to a user input made using the user interface, wherein the controller is configured to cause the switching arrangement to electrically connect one of the defroster and the first air treatment device to the power output of the RF signal source in response to the control signal.

10. The method of claim 1, further comprising:
activating a fan when the second RF signal is supplied to the first air treatment device.

11. A multifunctional radio frequency (RF) appliance comprising:
an RF signal source having a power output for supplying RF signals at multiple output frequencies;
a first air treatment device configured to be powered by a first RF signal at a first frequency;
a defroster configured to be powered by a second RF signal at a second frequency;
a switching arrangement configured to selectively electrically connect the first air treatment device and the defroster to the power output of the RF signal source; and
a controller configured to:
cause the switching arrangement to electrically disconnect the first air treatment device from the power output of the RF signal source and electrically connect the defroster to the power output of the RF signal source, and
cause the RF signal source to supply the second RF signal at the second frequency to the defroster.

12. The multifunctional RF appliance of claim 11, further comprising a variable impedance network having a first terminal connected to the switching arrangement and a second terminal coupled to the defroster.

13. The multifunctional RF appliance of claim 12, wherein the controller is configured to adjust an impedance of the variable impedance network to match an impedance of the RF signal source to an impedance of the defroster.

14. The multifunctional RF appliance of claim 11, wherein the controller is configured to cause the switching arrangement to electrically disconnect the first air treatment device from the power output of the RF signal source and electrically connect the defroster to the power output of the RF signal source according to a predetermine schedule.

15. The multifunctional RF appliance of claim 11, further comprising a user interface configured to transmit a control signal to the controller in response to a user input and wherein the controller is configured to cause the switching arrangement to electrically disconnect the first air treatment device from the power output of the RF signal source and electrically connect the defroster to the power output of the RF signal source in response to the control signal.

16. The multifunctional RF appliance of claim 11, further comprising:
a housing including a cavity configured to contain a load, wherein the first air treatment device is in fluid communication with the housing, and the defroster has an electrode at least partially disposed in the cavity.

17. The multifunctional RF appliance of claim 16, wherein the first air treatment device is selected from a plasma generator and an ultraviolet source situated in an air purification chamber.

18. The multifunctional RF appliance of claim 17, further comprising a fan disposed within the air purification chamber, the fan being connected to the controller and the controller being configured to activate the fan when the first RF signal at the first frequency is supplied to the first air treatment device.

19. The multifunctional RF appliance of claim 16, further comprising:
a second air treatment device in fluid communication with the housing, the second air treatment device being configured to receive a third RF signal at a third frequency, and to perform an air treatment process in response to the third RF signal, and wherein the controller is further configured to cause the switching arrangement to electrically connect the second air treatment device to the power output of the RF signal source.

20. A system comprising:
an RF signal source having a power output;
an air treatment device coupled to the power output of the RF signal source;
a defroster coupled to the power output of the RF signal source; and
a switching arrangement configured to selectively electrically connect the air treatment device to the power output of the RF signal source and to selectively electrically connect the defroster to the power output of the RF signal source,
wherein the RF signal source is configured to output a first RF signal at a first frequency while the air treatment device is electrically connected to the power output via the switching arrangement and is configured to output a second RF signal at a second frequency while the defroster is electrically connected to the power output via the switching arrangement.

* * * * *